United States Patent [19]

Lozeau et al.

[11] Patent Number: 5,688,497
[45] Date of Patent: Nov. 18, 1997

[54] SHAVING AID WITH PHYSIOLOGICAL COOLING EFFECT

[75] Inventors: Robert V. Lozeau, Madison; Manuel Andrade, Milford, both of Conn.

[73] Assignee: Warner-Lambert Company, Morris Plains, N.J.

[21] Appl. No.: 707,542

[22] Filed: Sep. 4, 1996

[51] Int. Cl.$^6$ ............................................. A61K 7/15
[52] U.S. Cl. ........................... 424/73; 424/401; 424/451
[58] Field of Search ............................ 424/73, 401, 451

[56] References Cited

U.S. PATENT DOCUMENTS

| | | | |
|---|---|---|---|
| 1,744,061 | 5/1930 | Salzberger. | |
| 2,134,666 | 2/1938 | Kritchevsky | 167/85 |
| 3,296,077 | 1/1967 | Berg | 167/85 |
| 3,839,220 | 10/1974 | Barchas | 252/305 |
| 3,949,067 | 4/1976 | Gibbs | 424/73 |
| 4,248,859 | 2/1981 | Rowsell et al. | 424/54 |
| 4,296,093 | 10/1981 | Rowsell et al. | 424/54 |
| 4,318,900 | 3/1982 | Rowsell et al. | 424/54 |

*Primary Examiner*—Thurman K. Page
*Assistant Examiner*—Murthy Sikha
*Attorney, Agent, or Firm*—Charles W. Almer

[57] ABSTRACT

Shaving aids are disclosed comprising at least one active ingredient which provides a physiological cooling effect.

4 Claims, No Drawings

SHAVING AID WITH PHYSIOLOGICAL COOLING EFFECT

The present invention is directed to shaving aids for use in wet shaving and, more particularly, to shaving aids which provide a physiological cooling effect.

BACKGROUND OF THE INVENTION

Various types of shaving aids are known in the razor industry. One popular type of shaving aid contains at least one water insoluble polymeric matrix and at least one water soluble material which exudes out of the insoluble matrix upon contact with water during shaving. Such shaving aids can be molded or extruded and then attached to razor heads mechanically, for example, with snap-in fittings or by molding the shaving aid into recesses containing anchors in a razor head. Such shaving aids are designed to exude the water soluble materials from the insoluble porous microstructure when the shaving aid becomes wet during shaving.

A number of different materials have been suggested for use as shaving aids. Previously suggested active ingredients include those disclosed in U.S. Pat. No. 4,170,821 to Booth, which is hereby incorporated by reference, and which can be used alone or in various combinations, such as:

A. A lubricating agent for reducing the frictional forces between a razor and the skin, e.g., a micro-encapsulated silicone oil.

B. An agent which reduces the drag between the razor parts and the shaver's face, e.g., a polyethylene oxide in the range of molecular weights between 100,000 and 6,000,000; a non-ionic polyacrylamide; and/or a natural polysaccharide derived from plant materials such as "guar gum".

C. An agent which modifies the chemical structure of the hair to allow the razor blade to pass through the whiskers very easily, e.g., a depilatory agent is one example.

D. A cleaning agent which allows the whisker and skin debris to be washed more easily from the razor parts during shaving, e.g., a silicon polyethylene oxide block copolymer and detergent such as sodium lauryl sulphate.

E. A medicinal agent for killing bacteria, or repairing skin damage and abrasions.

F. A cosmetic agent for softening, smoothing, conditioning or improving the skin.

G. A blood coagulant for the suppression of bleeding that occurs from nicks and cuts.

H. An astringent for constricting blood vessels thereby stemming the flow of bodily fluids such as lymph, which may exude from skin which has been irritated during shaving.

Alternatively, the shaving aid may comprise one or more of the shaving aids disclosed in U.S. Pat. No. 5,056,221 to Thoene, U.S. Pat. No. 4,044,120 to Rowsell et al., U.S. Pat. No. 5,095,619 to Davis et at., or Japanese Patent Application No. Hei 7 [1995]-24156 to Miyazaki, et al. which are also hereby incorporated by reference.

Those skilled in the art realize that shaving can result in unpleasant skin irritation. Such irritation may be discerned a short time after the skin surface has been shaved. A short time lapse between the shaving stroke and the unpleasant sensation is common, when such irritation occurs. Irritation of this type has previously been addressed with after shave treatments.

It would therefore be desirable to address and alleviate unpleasant sensations before the irritation is felt by the person shaving. It would therefore be desirable to provide at least one active ingredient which provides a physiological cooling effect to the area being shaved during the shaving process. An active ingredient which provides a physiological cooling effect during shaving has the ability to render an otherwise unpleasant experience into a favorable skin sensation.

SUMMARY OF THE INVENTION

The various embodiments of the present invention are directed to shaving aids comprising at least one active ingredient which provides a physiological cooling effect. The active ingredients which provide such cooling sensations may be utilized alone or in combination with one or more active ingredients which provide other desired effects.

The physiological cooling active ingredients of the present invention may be presented by the formula:

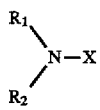

where $R_1$, when taken separately is H, $C_1$–$C_7$, alkyl or $C_3$–$C_6$ cycloalkyl;

$R_2$, when taken separately, is $C_3$–$C_8$ alkyl or $C_1$–$C_8$ alkylcycloatkyl, alkylcycloalkylalkyl, cyctoalkyl or cycloalkylalkyl, with the proviso that $R_2$ is branched at an alpha carbon atom relative to the N atom when R is H or at an alpha or beta carbon atoms when R is alkyl or cycloalkyl, this condition to be satisfied, in the case of cyclic groups, when the carbon atoms alpha or beta to the N atom is part of the cycle;

$R_1$ and $R_2$, when taken together, represent a straight or branched chain alkylene group forming with the N atom to which they are attached a 5–10 membered heterocycle, and preferably having branching at an alpha or beta carbon atom relative to the N atom.

$R_1$ and $R_2$, when separate groups and when taken together provide a total of at least 5 carbon atoms, and X represents $R_3CO$—, $R_4SO_2$—, or $R_5R_6 NCO$— where;

$R_3$ is H, $C_1$–$C_6$ alkyl, $C_3$–$C_6$ cycloalkyl, $C_2$–$C_8$ hydroxyalkyl, $C_2$–$C_8$ carboxyalkyl or $C_3$–$C_8$ alkylcarboxyalkyl with the proviso that when $R_3$ is $C_6$ alkyl it is primary in structure;

$R_4$ is $C_1$–$C_6$ alkyl or $C_3$–$C_6$ cycloalkyl, with the proviso that when $R_4$ is $C_5$ or $C_6$ alkyl it is primary in structure.

$R_5$ and $R_6$, when taken separately, are each H, $C_1$–$C_6$ alkyl, $C_3$–$C_6$ alkylcycloalkyl, cycloalkyl, or cycloalkylalkyl, $C_2$–$C_8$ hydroxyalkyl, $C_2$–$C_8$ carboxyalkyl or $C_3$–$C_8$ alkylcarboxyalkyl; or together represent a straight or branched chain $C_3$–$C_{10}$ alkylene group optionally containing an ether oxygen atom; and where:

$R_1$, $R_2$ and X provide a total of from 7–16 carbon atoms.

The physiologically cooling active ingredients of the present invention can be utilized with one or more active ingredients such as those set forth above or incorporated by reference herein.

DETAILED DESCRIPTION

According to the various embodiments of the present invention, at least one active ingredient having a physiological cooling effect is provided in a shaving aid. According to one preferred embodiment, an effective amount of an active ingredient providing a physiological cooling effect is disposed within a shaving aid along with a delivery system which will deliver at least a portion of the active ingredient to the skin surface during shaving.

For example, the physiologically cooling active ingredient of the present invention may be disposed either alone or with one or more active or inert ingredients in a water insoluble polymeric matrix in a manner which will allow the active ingredient(s) to exude from the shaving aid during shaving. Furthermore, the active ingredient of the present invention may be delivered utilizing the delivery system set forth in co-pending U.S. patent application Ser. No. 08/707, 437 filed on Sep. 4, 1996 which is hereby incorporated by reference. From the present description, those skilled in the art will appreciate that the advantages of the present invention can be obtained utilizing a variety of delivery systems which are suitable for use with shaving aids.

The compounds of formula I useful in providing physiological cooling effects in accordance with this invention fall into three classes: cyclic and acyclic amides, i.e. compounds of formula I, where X is $R_3CP-$,; substituted ureas, i.e. compounds of formula I where X is $R_5R_6NCO-$; and sulphonamides, i.e. compounds of formula I where X is $R_4SO_2-$. Of the three classes, the substituted ureas and the cyclic and acyclic amides are preferred over the sulphonamides by reason of generally higher levels of physiological cooling activity, greater stability and lower cost to manufacture. By reason of high levels of activity and lower expense, the substituted ureas are generally to be preferred over the cyclic and acyclic amides. The three classes of active compound will be discussed separately.

SUBSTITUTED UREAS

Broadly speaking the compounds of highest activity are the substituted ureas which may be represented by the formula II:

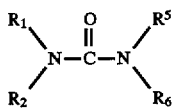

where $R_1$, $R_2$, $R_5$ and $R_6$ are as defined above. Preferred substituted ureas are those compounds where $R_1$ is H or $C_1$–$C_7$ alkyl, $R_2$ is $C_3$–$C_8$ alkyl or $C_3$–$C_8$ cycloalkyl, cycloalkylalkyl or alkylcycloalkyl, $R_2$ having branching in an alpha position relative to the N atom when $R_1$ is H, or at an alpha or beta position when $R_1$ is alkyl, or where $R_1$ and $R_2$ are joined to form an alkylene group having up to 10 carbon atoms and having branching at an alpha or beta position relative to the N atom, and forming together with the nitrogen atom a 5-, 6-, or 7- membered ring; and where $R_5$ is H or $C_1$–$C_6$ alkyl and $R_4$ is $C_1$–$C_6$ alkyl, or $C_3$–$C_6$ cycloalkyl, or where $R_5$ and $R_6$ jointly represent an alkylene group, optionally containing an ether oxygen atom and forming with the N atom a 5- or 6-membered ring.

The substituted ureas of formula II may be easily prepared by reaction of an appropriate amine with an isocyanate or carbamoyl chloride, the following being a typical reaction scheme:

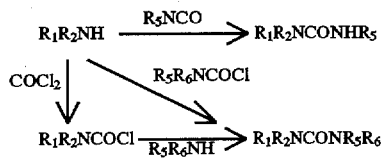

CYCLIC AND ACYCLIC AMIDES

The cyclic and acyclic amides useful in this invention may be represented by formula III:

where $R_1$, $R_2$ and $R_3$ are as defined above in connection with formula I. Preferred values for $R_1$ and $R_2$ are as set out above for formula II and the preferred values for $R_3$ are H, $C_1$–$C_6$ alkyl, $C_2$–$C_6$ hydroxyalkyl, carboxyalkyl or alkylcarboxyalkyl and $C_3$–$C_6$ cycloalkyl.

The amides may readily be prepared by reaction of the appropriate acid chloride and a substituted amine in accordance with procedures well known for the preparation of amides e.g.

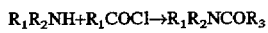

CYCLIC AND ACYCLIC SULPHONAMIDES

Although less preferred than the substituted ureas and amides hereinbefore described, but nevertheless still possessing utility in the compositions of this invention, are sulphonamides of formula IV:

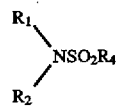

where $R_1$, $R_2$ and $R_4$ are as above defined in connection with formula I. Preferred values of $R_1$ and $R_2$ are as defined above in connection with formula II, and the preferred values for $R_4$ are $C_1$–$C_4$ alkyl.

The sulphonamides of formula IV may readily be prepared from the corresponding sulfonyl chloride and substituted amine by procedures well known in the art, e.g.

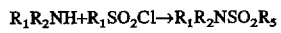

As will be apparent from the above formula, some of the compounds used as cold receptor stimulants in accordance with this invention exhibit either geometric or optical isomerism or both and, depending on the starting materials and the methods used in their preparation, the compounds may be isometrically pure, i.e. consisting of one geometric or optical isomer, or they may be isometric mixtures, both in the geometric and optical sense. Generally, the compounds will be used as isomeric mixtures, but in some cases the cooling effect may differ as between geometric or optical isomers, and therefore one or other isomer may be preferred.

What is claimed is:

1. A shaving aid comprising an effective amount of a compound capable of stimulating the cold receptors of the nervous system in the surface tissues of skin when brought into contact therewith, said compound having the formula:

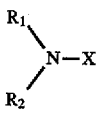

where $R_1$, when taken separately is H, $C_1$–$C_7$ alkyl or $C_3$–$C_6$ cycloalkyl;

$R_2$, when taken separately, is $C_3$–$C_8$ alkyl or $C_1$–$C_8$ alkylcycloalkyl, alkylcycloalkylalkyl, cycloalkyl or cycloalkylalkyl, with the proviso that $R_2$ is branched at an alpha carbon atom relative to the N atom when R is H or at an alpha or beta carbon atoms when R is alkyl or cycloalkyl, this condition to be satisfied, in the case of cyclic groups, when the carbon atoms alpha or beta to the N atom is part of the cycle;

$R_1$ and $R_2$, when taken together, represent a straight or branched chain alkylene group forming with the N atom to which they are attached a 5–10 membered heterocycle, and preferably having branching at an alpha or beta carbon atom relative to the N atom.

$R_1$ and $R_2$, when separate groups and when taken together provide a total of at least 5 carbon atoms, and X represents $R_3CO$—, $R_4SO_2$—, or $R_5R_6NCO$— where;

$R_3$ is H, $C_1$–$C_4$ alkyl, $C_3$–$C_4$ cycloalkyl, $C_2$–$C_4$ hydroxyalkyl, $C_2$–$C_8$ carboxyalkyl or $C_3$–$C_8$ alkylcarboxyalkyl with the proviso that when $R_3$ is $C_6$ alkyl it is primary in structure;

$R_4$ is $C_1$–$C_6$ alkyl or $C_3$–$C_6$ cycloalkyl, with the proviso that when $R_4$ is $C_5$ or $C_6$ alkyl it is primary in structure;

$R_5$ and $R_6$, when taken separately, are each H, $C_1$–$C_6$ alkyl, $C_3$–$C_6$ alkylcycloalkyl, cycloalkyl, or cycloalkylalkyl, $C_2$–$C_8$ hydroxyalkyl, $C_2$–$C_8$ carboxyalkyl or $C_3$–$C_8$ alkylcarboxyalkyl; or together represent a straight or branched chain $C_3$–$C_{10}$ alkylene group optionally containing an ether oxygen atom; and where:

$R_1$, $R_2$ and X provide a total of from 7–16 carbon atoms.

2. A shaving aid according to claim 1 wherein said compound has the formula:

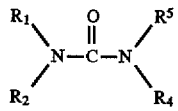

wherein $R_1$ is H, $C_1$–$C_7$ alkyl or $C_3$–$C_6$ cycloalkyl; $R_2$ is $C_3$–$C_8$ alkyl or $C_3$–$C_8$ cycloalkyl, alkylcycloalkyl, cycloalkylalkyl or alkylcycloalkylalkyl, with the proviso that when $R_1$ is H then $R_2$ is branched at an alpha carbon atom relative to the N atom, or at an alpha or beta carbon atom when $R_1$ is alkyl or cycloalkyl; and $R_5$ and $R_6$ are each H, $C_1$–$C_6$ alkyl, $C_3$–$C_6$ alkylcycloalkyl, cycloalkyl or cycloalkylalkyl, $C_2$–$C_8$ hydroxylalkyl, $C_2$–$C_8$ carboxyalkyl or $C_3$–$C_8$ alkylcarboxyalkyl;

$R_1$, $R_2$, $R_5$ and $R_6$ together providing a total of from 7–16 carbon atoms.

3. A shaving aid according to claim 1 further comprising an active ingredient selected from the group consisting of a lubricating agent, a medicinal agent, a vitamin, a cosmetic agent, a coagulant, an astringent, a cleaning agent, a skin conditioner, and blends thereof.

4. A shaving aid according to claim 1 wherein at least a portion of said compound is encapsulated in a cyclodextrin.

* * * * *